United States Patent
Barth et al.

(10) Patent No.: US 6,682,702 B2
(45) Date of Patent: Jan. 27, 2004

(54) APPARATUS AND METHOD FOR SIMULTANEOUSLY CONDUCTING MULTIPLE CHEMICAL REACTIONS

(75) Inventors: Phillip W. Barth, Portola Valley, CA (US); Douglas A. Amorese, Los Altos, CA (US); Carol T. Schembri, San Mateo, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 107 days.

(21) Appl. No.: 09/938,909

(22) Filed: Aug. 24, 2001

(65) Prior Publication Data

US 2003/0040011 A1 Feb. 27, 2003

(51) Int. Cl.$^7$ .................................................. B01L 3/00
(52) U.S. Cl. ........................ 422/102; 422/61; 422/68.1; 422/99; 436/37; 436/174; 436/177; 436/178
(58) Field of Search ............................ 436/34, 37, 63, 436/147, 162, 164, 166, 169, 174, 177, 178, 180; 422/61, 68.1, 99, 102

(56) References Cited

U.S. PATENT DOCUMENTS

| | | | |
|---|---|---|---|
| 3,873,268 A | * | 3/1975 | McKie, Jr. .................... 23/230 |
| 5,324,633 A | | 6/1994 | Fodor et al. |
| 5,356,751 A | * | 10/1994 | Cairncross et al. ......... 430/253 |
| 5,545,531 A | | 8/1996 | Rava et al. |
| 5,571,721 A | * | 11/1996 | Turner ..................... 435/305.1 |
| 6,054,100 A | * | 4/2000 | Stanchfield et al. ......... 422/102 |
| 6,083,763 A | | 7/2000 | Balch |
| 6,126,899 A | * | 10/2000 | Woudenberg et al. ......... 422/50 |
| 6,376,256 B1 | * | 4/2002 | Dunnington et al. ....... 436/178 |
| 6,376,619 B1 | * | 4/2002 | Halverson et al. ....... 525/330.3 |
| 6,395,483 B1 | * | 5/2002 | Patil et al. ..................... 435/6 |
| 6,410,332 B1 | * | 6/2002 | Desrosiers et al. .......... 436/37 |

FOREIGN PATENT DOCUMENTS

| | | |
|---|---|---|
| WO | WO 98/29736 | 7/1998 |
| WO | WO 00/72968 | 12/2000 |
| WO | WO 00/73766 | 12/2000 |

\* cited by examiner

*Primary Examiner*—Jill Warden
*Assistant Examiner*—Dwayne K Handy (57) ABSTRACT

A method and apparatus for simultaneously conducting multiple chemical reactions combine a test sample with a chemical reactant in a plurality of closed reaction chambers to produce reaction products. The method comprises assembling a plate having the test sample in a plurality of spatially arranged wells with a microarray of similarly spatially arranged surface bound chemical reactants to form the sealed apparatus having the plurality of closed reaction chambers. The apparatus is sealed such that it is gas, liquid and/or fluid tight. The seal may be accomplished with a flexible array substrate or a flexible gasket, and one or more of mechanical clamps, external fluid pressure, radiation, heat, vacuum and an adhesive. The sealed apparatus can be subjected to various reaction conditions, such as intense mechanical agitation and a controlled temperature environment. A kit comprises one or more of the elements of the apparatus.

49 Claims, 5 Drawing Sheets

APPARATUS AND METHOD FOR SIMULTANEOUSLY CONDUCTING MULTIPLE CHEMICAL REACTIONS

TECHNICAL FIELD

This invention relates to simultaneously reacting multiple chemical samples using arrays. In particular, the invention relates to an apparatus for and a method of conducting multiple chemical reactions or assays simultaneously using microarray technology for diagnostic, therapeutic and analytical applications.

BACKGROUND ART

Devices for processing multiple biological assays are known (U.S. Pat. Nos. 5,545,531 and 6,083,763, for example). The devices typically comprise reaction vessels having a plurality of reaction wells, each well has sidewalls and a closed end or bottom and an array of chemical samples fixed to the closed end. The end opposite to the closed end is open to access the reaction well for performing the assays with the array. Conventional microtiter plates are examples of conventional reaction vessels.

One conventional reaction vessel is made from a biochip wafer having a plurality of biological arrays fixed to the wafer surface and a microtiter-type plate attached to the wafer surface. The microtiter-type plate has a plurality of through holes formed completely through the thickness of the plate instead of closed-end wells as described above. The through holes in the microtiter-type plate are aligned with the plurality of arrays on the wafer. Reaction wells are formed by the attachment, wherein the wafer becomes the closed end and the through hole walls are the sidewalls of each reaction well. The arrays on the wafer are accessible via the open ends. Biological test samples are added to the open end to perform multiple assays at one time.

Another conventional reaction vessel is a conventional type of microtiter plate having a plurality of wells, wherein each well has sidewalls and a closed end. Individual biochips are attached inside each well. The individual biochips are obtained by dicing up the biochip wafer mentioned above. The individual biochips comprise an array of chemical samples fixed to a chip surface. The chip is adhered to the closed end of the well, such that the array surface of the chip is accessible from the open end of the well. Again, biological test samples are added to the open end to perform multiple assays at one time.

U.S. Pat. No. 5,324,633 discloses still another conventional reaction vessel that utilizes a flow cell having reservoirs that align with arrays of reactants on a substrate when the substrate is placed on the flow cell. Channels extending between the reservoir and the outside of the flow cell are used to inject the test sample into the reservoirs after the reaction vessel is assembled. O-rings are used to seal the substrate to the flow cell around each reservoir. Alternatively, the reaction vessel is a channel block having multiple channels therein. The channel block is mated with a substrate supporting arrays of biological material. The channels of the channel block are then filled with different reaction solutions that react with the arrays of biological materials similar to the flow cell.

The conventional reaction vessels are not self-contained (e.g., gas tight or fluid tight). Therefore, special handling and processing equipment must be used to perform assays using these conventional reaction vessels in order to provide stable handling and to control assay conditions, such as atmosphere, temperature, contamination, and prevent loss of sample or reagents, and the like. The special handling and processing equipment is expensive and not conducive to increased throughput, without added expense. Moreover, additional materials and assembly steps are needed if one skilled in the art wanted to seal the conventional reaction vessels to render them gas or fluid tight. For example, an additional cover plate or film must be placed over the open ends of the plurality of wells of the conventional reaction vessel to close or seal the open ends after the assay ingredients are added to the array therein. In the flow cell embodiments, the channels must be blocked with a cap or plug, for example, to seal the reservoirs.

Thus, it would be advantageous to have a method of simultaneously conducting multiple chemical reactions and a reaction vessel that is fully enclosed and gas, liquid and/or fluid tight without the need for cover plates and/or caps and the associated additional assembly steps. Such an apparatus and a method could decrease cost and increase throughput in the art of performing multiple assays.

SUMMARY OF THE INVENTION

The present invention provides a novel method of simultaneously conducting multiple chemical reactions and a reaction assembly apparatus that are low cost because the present invention can use pre-existing equipment, materials and well-known techniques to provide a self-contained, gas, liquid and/or fluid tight reaction vessel. In particular, the present invention is an apparatus for and a method of simultaneously conducting assays of multiple biological samples, such as assays of proteins, nucleic acids, specific binding pairs, and the like, advantageously that can use conventional microarrays and microtiter plates in a low cost manner for diagnostic, therapeutic and analytical applications, for example. The method and apparatus of the present invention can be subjected to handling and reaction conditions that are not available to the conventional reaction vessels described above. The handling and reaction conditions promote or accelerate the chemical reactions within the apparatus.

In one aspect of the invention, a method of simultaneously conducting multiple chemical reactions in a reaction assembly that comprises a microtiter plate of wells containing test samples and a microarray of sets of chemical reactants is provided. The method comprises the step of assembling the microarray of sets of chemical reactants to the microtiter plate of test samples such that the microarray covers open ends in the test sample wells of the microtiter plate to form a plurality of closed cells. Each closed cell comprises a set of chemical reactants and a respective test sample. The method further comprises the steps of sealing the microtiter plate to the microarray to create one or more of a gas, a liquid and a fluid tight seal; and mechanically agitating the sealed reaction assembly to contact test samples with the chemical reactants in each closed cell simultaneously.

In another aspect of the invention, a method of simultaneously conducting multiple chemical reactions between a first chemical sample and a second chemical sample is provided. The method comprises the step of providing a plate, having a plurality of spatially arranged wells in a well array pattern. Each well has a side wall adjacent to a closed end that enclose the well except for an open end opposite the closed end. The open end is adjacent to the plate surface for receiving a volume of the first chemical sample. The method further comprises the step of providing the second chemical sample bound to a surface of a substrate in an array pattern of features. The array of second chemical samples is spatially arranged in sets of features on the substrate surface similar in layout to the arrangement of the wells in the plate.

The method yet still further comprises the step of assembling the array and the plate into a reaction assembly and sealing the assembly. The array and plate are assembled such that the array substrate encloses the open ends of the plurality of wells in the plate. The features of the second chemical samples on the array are aligned with the open ends of the wells in the plate. Such aligned features and wells become multiple separate closed cells or reaction chambers in the reaction assembly. The reaction assembly is sealed to have one or more of a gas, liquid and fluid tight seal between the plate and the array, such that each closed cell is sealed.

The method yet still further comprises the step of simultaneously contacting the first chemical sample with the second chemical sample for a period of time in the plurality of closed cells to facilitate reactions therebetween. A variety of reaction parameters may be used for accomplishing the chemical reactions in accordance with the invention. Advantageously, the reaction assembly may be inverted and/or mechanically agitated under controlled temperature conditions to cause mixing between the first and second chemical samples in each closed cell.

In another aspect of the invention, an apparatus that provides for simultaneously conducting multiple chemical reactions is provided. The apparatus is a reaction assembly that comprises a plate having a plurality of spatially arranged wells in a well array pattern. Each well has a side wall adjacent to a closed end that enclose the well except for an open end opposite the closed end. The open end is adjacent to the plate surface for receiving a first sample into the wells. The apparatus further comprises an array comprising sets of a second sample bound to a surface of an array substrate in an array pattern of features. The sets of second samples are spatially arranged on the substrate surface similar in layout to the arrangement of the wells in the plate. Advantageously in one or more embodiments, the plate can be a conventional microtiter plate and the array can be a conventional microarray. The array is assembled to the plate, such that the array surface faces the plate surface, and such that the features on the array surface are aligned with the open ends in the plate. The array substrate covers the open ends of the wells in the plate to form a plurality of closed cells. Each closed cell comprises a respective set of second samples and a respective first sample. The apparatus further comprises a seal between the array substrate and the plate to provide one or more of a gas tight, a liquid tight and a fluid tight seal.

For the method and apparatus, the seal may be a seal formed by any one of using a flexible (pliable) array substrate and applying pressure, using a rigid or a flexible array substrate and an adhesive, using a pliable gasket between the array substrate and the plate and applying pressure, using the pliable gasket and an adhesive, and using a pliable gasket integral with the surface of the plate and applying pressure and/or using an adhesive. Pressure may be applied by one or more of mechanical clamps, external fluid pressure and vacuum, for example. Where an adhesive is used, one or more of heat, pressure and radiation may be used, but may be removed after the adhesive is cured or otherwise adhered to the surfaces.

In still another aspect of the invention, a kit for simultaneously conducting multiple assays of biological materials is provided. The kit comprises one or more of a plate having a plurality of wells spatially arranged in a surface of the plate, each well having a closed end, an open end opposite the closed end, and a side wall between the closed end and the open end; an array having a plurality of sets of biological features attached to one surface of an array substrate in a spatial arrangement similar to the well arrangement; a pliable gasket having a plurality of spatially arranged through holes, where the spatial arrangement of the through holes is similar to the spatial arrangement of the wells and the sets of biological features, and where the gasket is used to seal together the array and the plate; an adhesive for sealing together at least the array and the plate; and a sample of biological material as a control. The kit may optionally further comprise instructions for simultaneously conducting multiple assays according to the method of the present invention using the assembled reaction assembly apparatus of the present invention.

The reaction products produced by any of the above methods in the reaction assembly apparatus can be analyzed in accordance with the invention using well-known techniques and equipment. In one embodiment, the reaction products can be analyzed with the introduction of radiation into each closed cell, for example, through the plate or through the array substrate of the reaction assembly. In this embodiment, at least one of the plate or array substrates is transparent to the radiation, such as electromagnetic, particle, or ultrasonic radiation, which may be used in the evaluation of the reaction products. In another embodiment, the reaction assembly is disassembled to access the reaction products on the surface of the second substrate or array. In this embodiment, the surface may be rinsed to remove any unreacted test sample and prevent further reactions from occurring, before evaluation. In this embodiment, the array substrate may be transparent to the radiation used for analysis, or it may reflect or absorb the radiation used for analysis.

The apparatus and method of the present invention advantageously provide a reaction assembly to perform simultaneous multiple chemical reactions that uses the array substrate to cap or close the open ends of the wells in the plate. The reaction assembly is sealed using the material characteristics of the array substrate, a gasket, pressure and/or an adhesive to provide one or more of a gas, a liquid, or fluid tight seal. No other materials, such as conventional covers or caps, or assembly steps are necessary for the invention.

BRIEF DESCRIPTION OF THE DRAWINGS

The various features and advantages of the present invention may be more readily understood with reference to the following detailed description taken in conjunction with the accompanying drawings, where like reference numerals designate like structural elements, and in which.

MODES FOR CARRYING OUT THE INVENTION

Definitions

The following terms are intended to have the following general meanings as they are used herein, unless otherwise indicated below:

Gas—a substance or a mixture of substances, exhibiting zero surface tension and typically having low viscosity, including for example air, nitrogen, argon, helium, or superheated steam, and also including aerosols such as smoke and clouds of water vapor at a temperature less than the local boiling temperature for water. Gases are also considered herein to include gaseous plasmas containing charged particles.

Liquid—a substance or mixture of substances exhibiting surface tension and typically having higher viscosity than a gas, including for example water, oil, and liquid mercury. Liquids are also considered herein to include wet slurries containing finely divided powders in liquids.

Fluid—a substance exhibiting viscous flow characteristics, including both liquids and gases, and also including dry powders such as graphite, flour, and sand. A special case of a fluid is liquid helium exhibiting superfluid flow having zero viscosity.

Gas tight, liquid tight, and fluid tight seals—To be useful, a seal should be one or more of gas tight, liquid tight, and fluid tight against the flow of the particular substances to be contained by the seal. If gas tight against the flow of a particular gas, a seal will typically be tight also against the flow of liquids and powders. If liquid tight against the flow of a particular liquid, a seal may permit the flow of most gases. If fluid tight against the flow of a particular powder, a seal may permit the flow of most liquids and gases. However, a fluid tight seal can, at the extreme, be tight against the flow of all fluids including gases and liquids.

Nucleic acid—a high molecular weight material that is a polynucleotide or an oligonucleotide of DNA or RNA.

Polynucleotide—a compound or composition that is a polymeric nucleotide or nucleic acid polymer. The polynucleotide may be a natural compound or a synthetic compound. In the context of an assay, the polynucleotide can have from about 20 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA, double-stranded or single-stranded (dsDNA and ssDNA), and RNA, including t-RNA, m-RNA, r-RNA, mitochondrial DNA and RNA, chloroplast DNA and RNA, complementary DNA (cDNA) (a single stranded DNA that is complementary to an RNA and synthesized from the RNA in vitro using reverse transcriptase), DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, and the like.

Polynucleotides include analogs of naturally occurring polynucleotides in which one or more nucleotides are modified over naturally occurring nucleotides. Polynucleotides then, include compounds produced synthetically (for example, PNA as described in U.S. Pat. No. 5,948,902 and the references cited therein, all of which are incorporated herein by reference), which can hybridize in a sequence specific manner analogous to that of naturally occurring complementary polynucleotides.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site-specific chemical cleavage method.

For purposes of this invention, the polynucleotide, or a cleaved fragment obtained from the polynucleotide, will usually be at least partially denatured or single-stranded or treated to render it denatured or single-stranded. Such treatments are well known in the art and include, for instance, heat or alkali treatment, or enzymatic digestion of one strand. For example, double stranded DNA (dsDNA) can be heated at 90–100° C. for a period of about 1 to 10 minutes to produce denatured material, while RNA produced via transcription from a dsDNA template is already single-stranded.

Oligonucleotide—a polynucleotide, usually single-stranded, usually a synthetic polynucleotide but may be a naturally occurring polynucleotide. The oligonucleotide(s) are usually comprised of a sequence of at least 5 nucleotides, usually, 10 to 100 nucleotides, preferably 20 to 60 nucleotides, and more preferably 25 to 60 nucleotides in length.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single-stranded DNA as described in J. Messing (1983) *Methods Enzymol.* 101:20-78.

Other methods of oligonucleotide synthesis include phosphotriester and phosphodiester methods (Narang, et al., (1979) *Meth. Enzymol.* 68:90) and synthesis on a support (Beaucage, et al. (1981) *Tetrahedron Letters* 22:1859–1862) as well as phosphoramidite techniques (Caruthers, M. H., et al., "Methods in Enzymology," Vol. 154, pp. 287–314 (1988) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., *Proc. Nat. Aca. Sci. USA* (1994) 91:5022–5026. Unless otherwise noted herein, the terms nucleic acid, oligonucleotide and polynucleotide are intended to be used interchangeably.

Nucleotide—the monomeric unit of nucleic acid polymers, i.e., DNA and RNA, whether obtained from a natural source or produced synthetically, which comprises a nitrogenous heterocyclic base, which is a derivative of either a purine or pyrimidine, a pentose sugar, and a phosphate (or phosphoric acid). When the phosphate is removed, the monomeric unit that remains is a "nucleoside". Thus a nucleotide is a 5'-phosphate of the corresponding nucleoside. When the nitrogenous base is removed from the nucleotide, the monomeric unit that remains is a "phosphodiester". For the purposes of the invention, "nucleotide" includes its corresponding nucleoside and phosphodiester, and "oligonucleotide" includes its corresponding oligonucleoside and oligophosphodiester, unless indicated otherwise. The term "nucleotide" includes "modified nucleotide" that contains a modified base, sugar or phosphate group. The modified nucleotide can be produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach, a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth.

Target—a compound to be identified, such as a test sample. In nucleic acid assays, a target is usually existing within a portion or all of a polynucleotide, usually a polynucleotide analyte. The identity of the target nucleotide sequence generally is known to an extent sufficient to allow preparation of various probe sequences hybridizable with the target material.

The target material usually contains from about 20 to 5,000 or more nucleotides, preferably 30 to 1,000 nucleotides. The target material is generally a fraction of a larger molecule or it may be substantially the entire molecule such as a polynucleotide as described above. The minimum number of nucleotides in the target material is selected to assure that the presence of a target polynucleotide in a sample is a specific indicator of the presence of polynucleotide in a sample. The maximum number of nucleotides in the target material is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

Probe—a compound used to evaluate a target, such as a chemical reactant. In nucleic acid assays, the probe is an oligonucleotide or polynucleotide employed to bind to a portion of a polynucleotide such as another oligonucleotide or a target material. The design and preparation of the nucleic acid probes are generally dependent upon the sensitivity and specificity required, the sequence of the target material and, in certain cases, the biological significance of certain portions of the target material.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. For the purposes of the invention, hybridization of complementary Watson/Crick base pairs of probes on the microarray and of the target material is preferred, but non Watson/Crick base pairing during hybridization may also occur.

Conventional hybridization solutions and processes for hybridization are described in J. Sambrook, E. F. Fritsch, T. Maniatis, *Molecular Cloning: A Laboratory Manual,* Cold Spring Harbor Laboratory Press, Cold Spring Harbor, Ed. $2^{nd}$, 1989, vol. 1–3, incorporated herein by reference. Conditions for hybridization typically include (1) high ionic strength solution, (2) at a controlled temperature, and (3) in the presence of carrier DNA and surfactants and chelators of divalent cations, all of which are well known in the art.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence, to form Watson/Crick base pairs. RNA sequences can also include complementary G=U or U=G base pairs. Non-standard or non Watson/Crick base pairing is also possible with nucleotide complements, for instance, the sequences may be parallel to each other and complementary A=C or G=U base pairs in RNA sequences or complementary G=T or A=C base pairs in DNA sequences may occur, although are not preferred.

Substrate or surface—a porous or non-porous support material, preferably a reaction solvent-insoluble support material. The surface can have any one of a number of shapes, such as strip, plate, disk, rod, particle, including bead, and the like. The substrate can be hydrophobic or hydrophilic or capable of being rendered hydrophobic or hydrophilic and includes inorganic powders such as silica, magnesium sulfate, and alumina; natural polymeric materials, particularly cellulosic materials and materials derived from cellulose, such as fiber-containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly (vinyl butyrate), etc.; either used by themselves or in conjunction with other materials; glass available as Bioglass, ceramics, metals, anodized metal surfaces, semiconductors, coated semiconductor surfaces, and the like. Natural or synthetic assemblies such as liposomes, phospholipid vesicles, and cells can also be employed.

Common substrates used for microarrays are surface-derivatized glass or silica, or polymer membrane surfaces, as described in Z. Guo et al. (cited above) and U. Maskos, E. M. Southern, *Nucleic Acids Res.* 20, 1679–84 (1992) and E. M. Southern et al., *Nucleic Acids Res.* 22, 1368–73 (1994), both incorporated herein by reference. In modifying siliceous or metal oxide surfaces, one technique that has been used is derivatization with bifunctional silanes, i.e., silanes having a first functional group enabling covalent binding to the surface (often an Si-halogen or Si-alkoxy group, as in $SiCl_3$ or $-Si(OCH_3)_3$, respectively) and a second functional group that can impart the desired chemical and/or physical modifications to the surface to covalently or non-covalently attach ligands and/or the polymers or monomers for the biological probe array. See, for example, U.S. Pat. No. 5,624,711 to Sundberg, U.S. Pat. No. 5,266,222 to Willis and U.S. Pat. No. 5,137,765 to Farnsworth, each incorporated herein by reference.

Immobilization of oligonucleotides on a substrate or surface may be accomplished by well-known techniques, commonly available in the literature. See, for example, A. C. Pease, et al., *Proc. Nat. Acad. Sci. USA*, 91:5022–5026 (1994); Z. Guo, R. A. Guilfoyle, A. J. Thiel, R. Wang, L. M. Smith, *Nucleic Acids Res.* 22, 5456–65 (1994); and M. Schena, D. Shalon, R. W. Davis, P. O. Brown, *Science,* 270, 467–70 (1995), each incorporated herein by reference. Substrates may be purchased with a coating, or coated, with an adsorbed polymer to facilitate linking to the surface. See for example, web site http://cmgm.stanford.edu/pbrown/protocols/1_slides.html for conventional coating protocols.

Feature—a feature is either a probe/chemical reactant or a target/chemical test sample bonded to an array substrate. The location of a feature is addressable, typically by a row and column location, or other spatial address. A feature may include a plurality or a set of 'subfeatures', where each set is a 'subarray'. For the purposes of the invention, there is a plurality of features on an array or microarray, where each feature comprises a plurality of subfeatures. However, the term 'microarray' may be characterized by some skilled in the art as comprising one or more of the subarrays of a larger array. For the purposes of the invention, the terms 'array' and 'microarray' are used interchangeably herein unless specified otherwise.

Label—a member of a signal producing system. Usually the label is part of a target or a probe, either being conjugated thereto or otherwise bound thereto or associated therewith. The label is capable of being detected directly or indirectly. Labels include (i) reporter molecules that can be detected directly by virtue of generating a signal, e.g., a fluorophore, (ii) specific binding pair members that may be detected indirectly by subsequent binding to a cognate that contains a reporter molecule, e.g., biotin-streptavidin, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. Labels further include but are not limited to radioactive, magnetic, quantum dot labels or tags, or the like. In general, any reporter molecule that is detectable can be used. For example, the nucleic acid base is modified to include biotin, which binds to streptavidin that has been previously covalently linked to a fluorophore. Direct labels are commercially available from several manufacturers, including Boehringer-Mannheim and Amersham-Pharmacia Biotech. Boehringer-Mannheim also sells biotinylated nucleotides, and Amersham-Pharmacia Biotech also sells streptavidin labeled with a variety of fluorophores.

The reporter molecule can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label can generate a detectable signal either alone or together with other members of the signal producing system. As mentioned above, a reporter molecule can be bound directly to a nucleotide sequence or can become bound thereto by being bound to an specific binding pair (sbp) member complementary to an sbp member that is bound to a nucleotide sequence. Examples of particular labels or reporter molecules and their detection can be found in U.S. Pat. No. 5,508,178, the relevant disclosure of which is incorporated herein by reference. When a reporter molecule is not conjugated to a nucleotide sequence, the reporter molecule may be bound to an sbp member complementary to an sbp member that is bound to or part of a nucleotide sequence.

Signal Producing System—the signal producing system may have one or more components, at least one component being the label. The signal producing system generates a signal that typically relates to the presence or amount of a target in a medium. The signal producing system includes all of the reagents required to produce a measurable signal. Other components of the signal producing system may be included in the developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Signal-producing systems that may be employed in the present invention are those described more fully in U.S. Pat. No. 5,508,178, the relevant disclosure of which is incorporated herein by reference.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as cognates or as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Detailed Description

The present invention is a novel method of simultaneously conducting multiple chemical reactions that is low cost and an apparatus for conducting the multiple chemical reactions. The present method and apparatus can use pre-existing materials, equipment and well-known techniques to assemble a fully enclosed, gas, liquid and/or fluid tight reaction vessel apparatus having multiple closed reaction chambers that can be subjected to reaction conditions that accelerate chemical reactions, such as intense mechanical agitation, or otherwise inverting the vessel for mixing reactants under controlled temperature.

Advantageously, the results of the multiple chemical reactions according to the present invention can be analyzed while the reaction vessel apparatus is fully assembled. Further the present invention provides for the reaction vessel to be disassembled for analysis of reaction products. The present invention is particularly useful in the art of biological assays of genes, gene components and products, nucleic acids, proteins, antibodies and antigens, ligands and receptors, or the like, for diagnostic, therapeutic and analytical applications, for example. The method and apparatus of the present invention advantageously can use conventional microarrays and microtiter plates in a low cost manner for multiplexing chemical reactions in a gas and/or liquid and/or fluid tight reaction assembly.

Therefore, the present invention is a method of simultaneously conducting multiple chemical reactions and a reaction assembly apparatus that comprises a plate of wells containing test samples, an array of sets of chemical reactants, and a seal between the plate and the array to create a plurality of sealed reaction cells, which is gas, liquid and/or fluid tight. The method comprises the steps of assembling the array of sets of chemical reactants to the plate of test samples, such that the array covers open ends in the test sample wells of the plate to form a plurality of closed cells. Each closed cell comprises a set of chemical reactants and a respective test sample. The method further comprises the steps of sealing the plate to the array to create one or more of a gas tight, a liquid tight, and a fluid tight seal; and contacting the test samples with the chemical reactants in each closed cell of the sealed reaction assembly simultaneously, such as by mechanical agitation, to facilitate any reaction between the chemical reactants and test samples. The details of the method and apparatus of the present invention are described further below with respect to specific embodiments.

Figure 1:
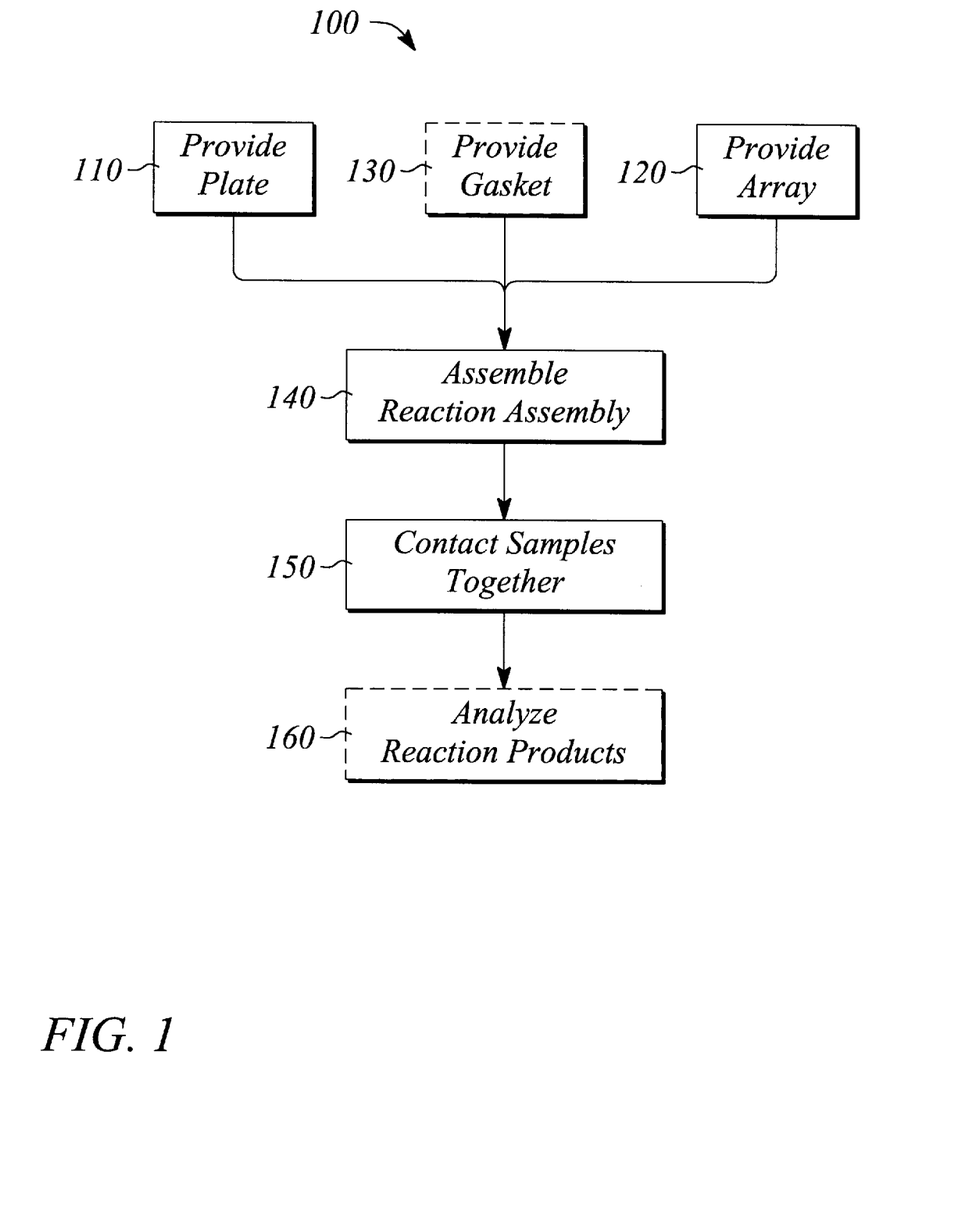
FIG. 1 illustrates a flow chart of one embodiment of the method of the present invention.
Figure 2:
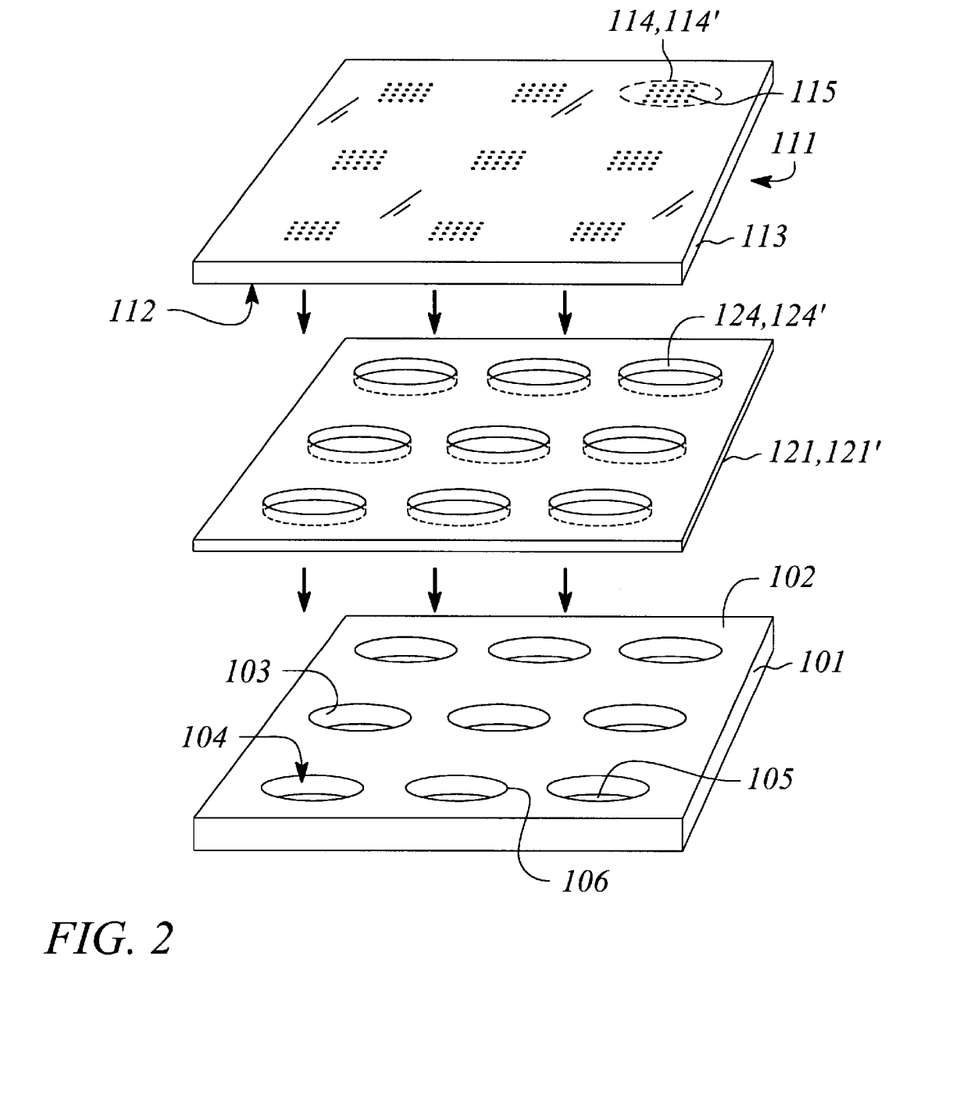
FIG. 2 illustrates the components and the assembly direction of the reaction assembly in accordance with a preferred embodiment of the present invention.

In one aspect of the invention, a method 100 of simultaneously conducting multiple chemical reactions between a first chemical sample and a second chemical sample is provided. A flow chart of the method 100 is illustrated in FIG. 1. The method 100 comprises the step of providing 110 a plate 101 having a plurality of wells 104 in a surface 102 of the plate 101 that are separated by a well spacing. The wells are arranged in an array pattern. FIG. 2 schematically illustrates the plate 101. Each well 104 extends in a thickness dimension of the plate and has a side wall 103 adjacent to a closed end 105 that together enclose all sides of the well except for an open end 106 opposite the closed end 105. The open end 106 is adjacent to the surface 102 of the plate 101 to provide access to the well 104 for receiving a volume of the first chemical sample. The first chemical sample in each well 104 may be the same, or may be different in at least one well 104 of the plate 101. Preferably, the first chemical sample has different characteristics to be evaluated in different wells. A gas volume occupies any space in each well 104 that is not occupied by the first chemical sample. A standard microtiter plate, having 96, 384, or 1536 wells, or a 9×26 plate having 234 wells on 2.25 mm centers, for example, is preferred for the plate 101 of the present method 100.

The method 100 further comprises the step of providing 120 an array 111 of the second chemical sample bound to a surface 112 of an array substrate 113 in an array pattern of features 114. The array 111 also is schematically illustrated in FIG. 2. The array 111 of second chemical samples has an array or feature spacing that is similar to the well spacing of the plate 101. In a preferred embodiment, the features 114 of the array 111 are organized into sets or subarrays 114' of the second chemical sample. Each subarray 114' comprises an addressable matrix of subfeature 115 locations, for example, of the second chemical sample. The matrix may be rectangular, circular or other overall shape, as along as the subfeatures 115 are addressable. The subarrays 114' are arranged relative to each other to have the array spacing. The subfeatures 115 in each subarray 114' have a subfeature spacing that is a fraction of (or much less than) the array spacing. The second chemical sample at each location 114 on the array 111 or in each subarray 114' can be the same, or can be different in at least one location 114 on the array 111 or in at least one subarray 114' or at least one subfeature 115 within a subarray 114'. Preferably, the second chemical sample provides different characteristics to evaluate the first chemical sample at different array or different subarray locations. The array substrate 113 and the array pattern are sized, shaped and arranged to interface with the plate 101 and well array pattern. The array substrate 113 is preferably optically transparent and is illustrated in FIG. 2 in an inverted position (surface 112 facing toward the plate 101) with the array of features 114, 114' visible through the optically transparent substrate 113.

Figure 3:
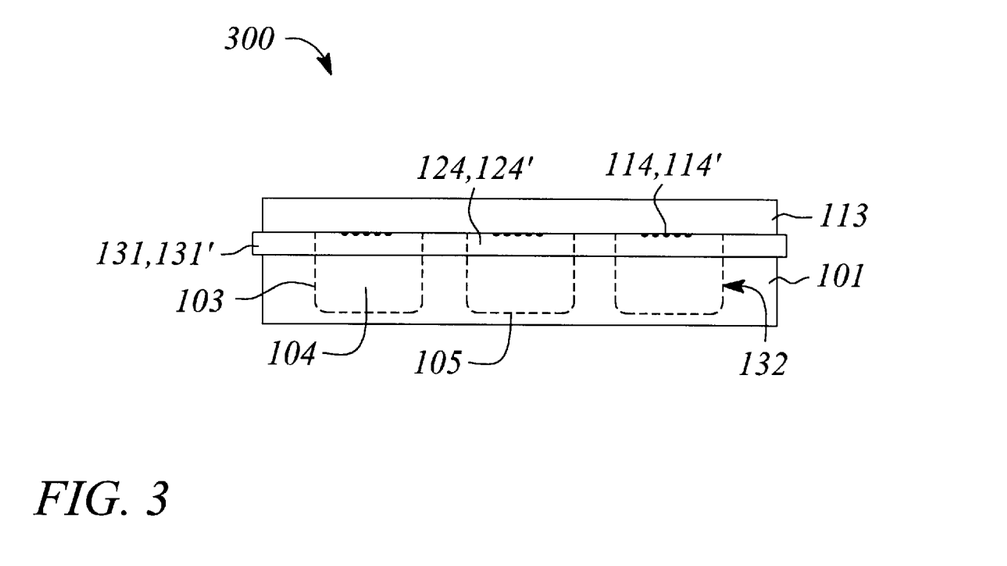
FIG. 3 illustrates a side view of the reaction assembly in accordance with the present invention.

The method 100 still further comprises the step of assembling 140 together the array 111 and the plate 101 to form the reaction assembly apparatus 300, according to the present invention, illustrated in FIG. 3. The array substrate 113 is placed on the plate 101, such that the array surface 112 is adjacent to the plate surface 102 and the features 114, 114' are aligned with the open ends 106 of the wells 104. The array substrate 113 and the plate 101 are then sealed to provide the reaction assembly apparatus 300 having individual closed chambers 132 at each well 104 location that are gas and/or liquid and/or fluid tight. The seal 131, 131' can be accomplished in several ways according to the invention, depending on the embodiment.

In one embodiment, the seal 131 comprises using an array substrate 113 that is flexible and pliable, and further, applying pressure to the assembly with one or more of mechanical clamps, external fluid pressure and vacuum, for example, to contact the flexible array substrate 113 with the plate 101 to form the reaction assembly apparatus 300. In another embodiment, the array substrate 113 is a flexible material or film and comprises an adhesive surface. The adhesive surface may be an adhesive coating that is applied uniformly, such that the coating underlies the features 114 of array 111 and does not interfere with array processing and analysis. Alternatively, the adhesive coating may be applied by silk screening and/or masking, such that the area in contact with the array of second chemical sample features does not have adhesive. As another alternative, the adhesive surface may be an adhesive coating that is applied uniformly, such that the coating overlies the features 114 of array 111 and permits sufficient transmission of the first sample through the adhesive coating to the features 114 of the array 111 and such that the adhesive does not interfere with array processing, chemical reactions and analysis. The adhesive on the surface 112 surrounds the feature 114, 114' locations and provides a seal 131 around each open end 106 of the wells 104 by applying heat, pressure and/or radiation, as mentioned above.

The adhesive characteristics are compatible with the substrate 113 material, especially under the conditions of the assay. Ultraviolet light curable adhesives, which have increased adhesion or bond strength with the application of ultraviolet (UV) light, are one type of adhesive that can be used with the present invention. Such UV curable adhesives include, but are not limited to, Dymax UV cure adhesives from Dymax Corporation, Torrington, Conn. Releasable adhesives, i.e., adhesives that have reduced adhesion with the application of heat, cold or radiation, are particularly advantageous in an embodiment of the method 100, where the apparatus 300 is later disassembled, as described below.

UV releasable adhesives have reduced adhesion when exposed to UV light. Adwill D-Series UV curable dicing tape from LINTEC Corp. of Japan; Furukawa UV-Tape from The Furukawa Electric Co, Ltd. of Japan; and Wacker UV-Tape for Wafer dicing available from Dou Yee Enterprises of Singapore are examples of flexible tapes with UV releasable adhesives that might work with the preferred embodiment of the invention. UV releasable adhesives are also sometimes commonly called UV curable adhesives, leading to possible confusion between adhesives whose adhesion decreases on exposure to UV light and adhesives whose adhesion increases on exposure to UV light. In this document, a 'UV curable' adhesive means one whose adhesion increases on exposure to UV light, and a 'UV releasable' adhesive means one whose adhesion decreases on exposure to UV light, unless otherwise stated.

Alternatively, the flexible film with an adhesive surface embodiment of the array substrate 113 may use the same adhesive that is used for the ABI Prism® Optical Adhesive Cover from PE Corporation. See for example, web site http://www.hmc.psu.edu/core/Genetics%20Core/RealTime_PCR/UsingOpticalAdhesiveCovers.pdf. The ABI Prism® Optical Adhesive Cover is essentially an optically transparent flexible film tape that has an adhesive surface protected with a protective backing that is peeled away for attachment to a conventional microtiter plate or conventional reaction assembly. For the invention, the ABI Prism® Optical Adhesive Cover could be adapted for use as the array substrate 113, wherein the protected surface could be modified, such that the protected surface would be the array surface 112 and the areas corresponding to the array of features 114, 114' would be rendered non-adhesive. The second chemical samples could be bound to the non-adhesive areas. This modified optical adhesive tape substrate 113 would be assembled on the plate 101 to form a seal 131 in accordance with the manufacturers instructions, for example as provided on the web site. Alternatively, the same adhesive used for the ABI Prism® Optical Adhesive Cover could be uniformly placed on the surface of a flexible tape, and the features 114 of array 111 could overlie the adhesive. As a further alternative, the adhesive used for the ABI Prism® Optical Adhesive Cover could be placed on a rigid substrate 113, either only in sealing areas, which are removed from the areas of features 114, or in a uniform film underlying both the sealing areas and the areas of features 114.

Figure 5:
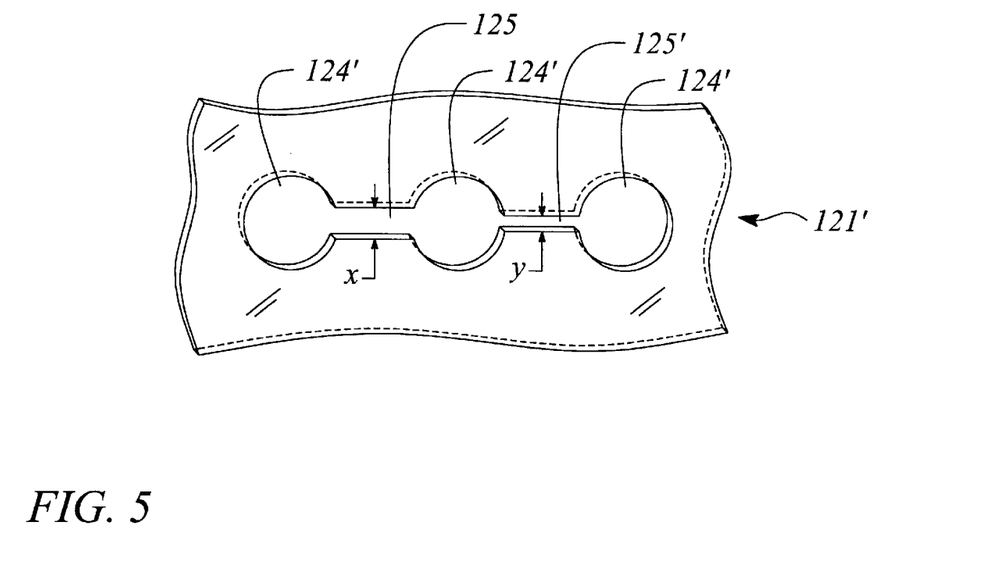
FIG. 5 illustrates a magnified partial top view of one embodiment of the gasket illustrated in FIG. 2.
Figure 6:
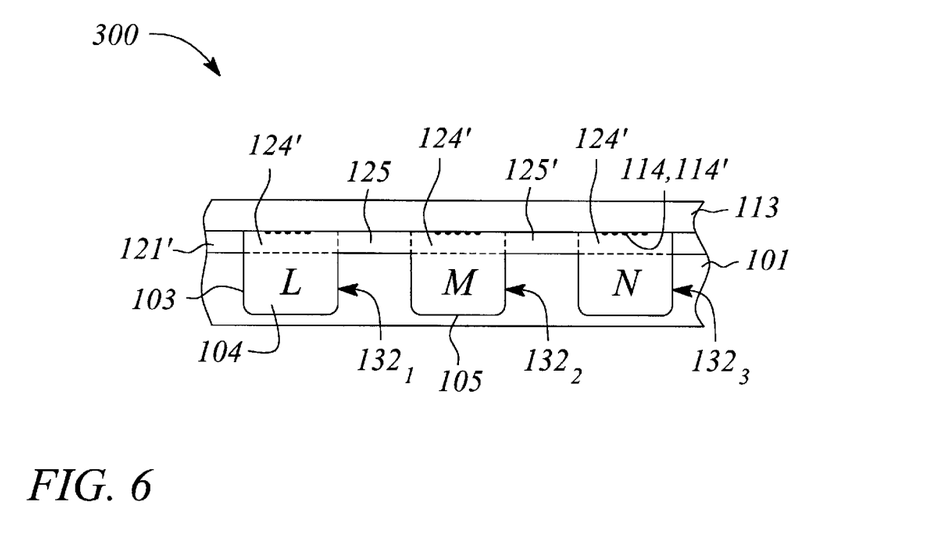
FIG. 6 illustrates a side view of the reaction assembly that uses the gasket illustrated in FIG. 5 in another embodiment of the present invention.

In still another embodiment, the seal 131, 131' may comprise using any conventional substrate material for the array substrate 113 and further using a flexible and/or pliable gasket 121, 121' between the array substrate 113 and the plate 101, as is illustrated in FIGS. 2, 5 and 6 and as further described below with reference to a method 200. The conventional array substrate 113 is basically nonreactive in the chemical reactions between the chemical samples, and preferably is optically transparent, such as silica glass, soda lime glass, or a polymeric material, all such materials being well known in the art and further defined in the Definitions section. The gasket 121, 121' has a plurality of through holes 124, 124' in a through hole pattern that is similar to and aligns with the feature array pattern and the well array pattern. In yet another embodiment, the pliable gasket material may be integral to the surface 102 of the plate 101. In both gasket embodiments, a seal 131, 131' is made by applying pressure to compress the gasket material against the substrate 113 and the plate 101 using one or more of mechanical clamps, external fluid pressure and vacuum, for example. As further described below with reference to method 200, the gasket 121, 121' may comprise an adhesive surface and the seal 131, 131' is made by further applying one or more of radiation, heat and cold.

FIG. 2 illustrates only nine features 114, 114', wells 104 and gasket through holes 124, 124' for simplicity. As mentioned herein, the array pattern of features 114, 114' for the method of conducting multiple chemical reactions may be that provided by a 96, 234, 384, or 1536 well microtiter plate, or larger, for example. The number of features 114, 114' is dictated by the number of wells in the plate. The number of subfeatures 115 in a feature 114, 114' is limited by the minimum available spacing of individual subfeatures 115, and possibly by the array fabrication techniques and equipment used, and further, is dictated by the size of the opening 106 in each well of the plate 101. Only 20 subfeatures 115 per subarray 114' or feature 114 are illustrated in FIG. 2 for simplicity only. These illustrations are not meant to limit the scope of the invention in any way.

The method 100 still further comprises the step of simultaneously contacting 150 the first chemical sample with the second chemical sample for a period of time in the plurality of closed cells or chambers 132 formed by the assembly 140 of the apparatus 300. The step of contacting 150 facilitates any reactions that may occur between the first chemical sample and the second chemical sample. The reaction parameters used in the step of contacting 150 vary and depend on the chemical samples used and reaction conditions needed for accomplishing the chemical reactions. In one embodiment, the step of contacting 150 comprises inverting the reaction assembly apparatus 300, such that the first chemical sample in each well 104 may contact the second chemical sample on a respective aligned feature 114, 114' in the closed cell 132. Gravity will tend to pull the first chemical sample volume of each well 104 into contact with the respective aligned feature 114, 114' of second chemical sample. In another embodiment, the step of contacting 150 comprises taking the reaction assembly apparatus 300 to a desired reaction temperature, which is maintained for the period of time. The reaction assembly apparatus 300 may or may not be inverted when the temperature is changed. In still another embodiment, the reaction assembly apparatus 300 is mechanically agitated to facilitate mixing and/or chemical reactions within each closed cell 132. Mechanical agitation is further described below with respect to method 200. Again, the reaction assembly apparatus 300 may or may not be inverted for the step of agitation. In yet still another embodiment, the reaction assembly apparatus 300 is inverted, taken to the desired reaction temperature for the period of time and mechanically agitated to provide optimum mixing and reaction conditions. Mechanical agitation can decrease the reaction time without loss of sample in the reaction assembly apparatus 300 of the present invention.

Preferably, the chemical reactions are quenched after the reaction time period. The step of quenching can comprises removing the reaction temperature, where a temperature change was applied; or stopping the mechanical agitation where agitation was applied; or both removing and stopping, where both temperature and agitation were applied, for example. In one embodiment, the step of quenching further comprises disassembling the reaction assembly apparatus 300 and rinsing the surface 112 of the reacted array 111. Rinsing the array surface 112 will remove any unreacted first chemical sample and prevent further reactions from occurring. The materials and methods used for rinsing the reacted array 111 are well known in the art. Advantageously according to some embodiments, the reaction assembly apparatus 300 of the present invention may be disassembled without damage to the parts. Where pressure was used to form the seal 131, 131', the apparatus 300 disassembly is a matter of removing the pressure source. Where a UV releasable adhesive was used to form the seal 131, 131', the apparatus 300 disassembly comprises applying UV light to the adhesive to release the array substrate 113 from the plate 101. Depending on the nature of the first and second samples, it may be necessary to use a shadow mask to shield the features 114, 114' from the UV light source during the application of UV light. Such a shadow mask can take the form of, for example, thin film chrome shadowing features on a transparent fused quartz plate, which is well known to those skilled in photolithographic techniques for the semiconductor circuit fabrication art.

In a preferred embodiment, the method 100 further comprises the step of analyzing 160 the array 111. The array 111 may be analyzed 160 after the apparatus 300 is disassembled and the array surface 112 is rinsed. Alternatively, the array 111 advantageously can be analyzed 160 while the reaction assembly apparatus 300 is still assembled, as long as either the array substrate 113 or the plate 101 is transparent to the radiation used for analysis, or if a radioactive source is used and the array substrate 113 is thin. The step of analyzing 160 comprises interrogating the array 111 and processing data collected as a result of the interrogation. The array 111 is analyzed 160 to determine information about any reaction products on the surface 112 of the reacted array 111.

Typically, analysis is performed with automated equipment that can address the feature 114 locations (and subfeature locations 115 in a subarray 114') individually, sequentially and/or simultaneously to evaluate any reaction products at each location. The automated equipment may include a radiation source and detector interfaced with a computer or microprocessor that provides for scanning the array 111. The radiation source is used to interrogate the array 111. The radiation source may emit electromagnetic, radioactive particle, or ultrasonic radiation, for example. Typically, either the first chemical sample or the second chemical sample will be labeled with a label or tag that emits a signal when scanned or interrogated with the particular radiation source. Conventional labeling materials and techniques that are well-known in the art can be used to label the chemical samples in accordance with the invention (also see Definitions section above). Further, conventional scanning equipment that is well-known in the art can be used for the invention, for example the GENEARRAY scanner manufactured by Agilent Technologies, Inc. of Palo Alto, Calif. (also see e.g., web site http://www.bioelectrospec.com or http://barolo.ipc.uni-tuebingen.de/infomat/tirf/rianaindex_en.html for information on 'total internal reflection fluorescence' (TIRF), which may be used in the analysis aspect of the present invention). Alternatively, if a radioactive label such as phosphorous is used to label the first chemical sample, for example, a phosphor imager such as one of those manufactured by Packard Instruments or Fujifilm or Molecular Dynamics or others may be used, and an external radiation source is not needed. However, it is not the intent of the inventors to be limited to any particular labeling system and scanning equipment. All labeling systems and scanners known in the art are within the scope of the invention.

The scanning system will interrogate and process signal data obtained from scanning the tags present on the array 111 after the step of contacting 150. The radiation will elicit responses or signals from the labeled reaction products, which are detected by the detector and analyzed by the computer or microprocessor. The intensity of each signal and its locations on the array 111 will provide valuable information about the chemical samples and reaction products.

According to the preferred embodiment, the step of contacting 150 comprises exposing the biological materials in the reaction assembly apparatus 300 to hybridization or binding conditions known in the art. Advantageously, the reaction assembly apparatus 300 of the present invention can be exposed to intense mechanical agitation without loss of sample to accelerate any reactions between biological materials under a controlled temperature in accordance with the method 100.

In another aspect of the invention, a method 200 of simultaneously conducting multiple different chemical reactions between a plurality of chemical reactants and a plurality of test chemical samples is provided. For this embodiment, either or both of the plurality of chemical reactants and the plurality of test chemical samples, respectively, may comprise at least one reactant that is different from the others, or may comprise at least one test sample that is different from the others. The chemical reactants are defined herein as being used to evaluate the test chemical samples. Therefore, which of the chemical reactants or test samples are different and how they differ is a function of the evaluation to be performed and not a limitation to the present invention.

Figure 4:
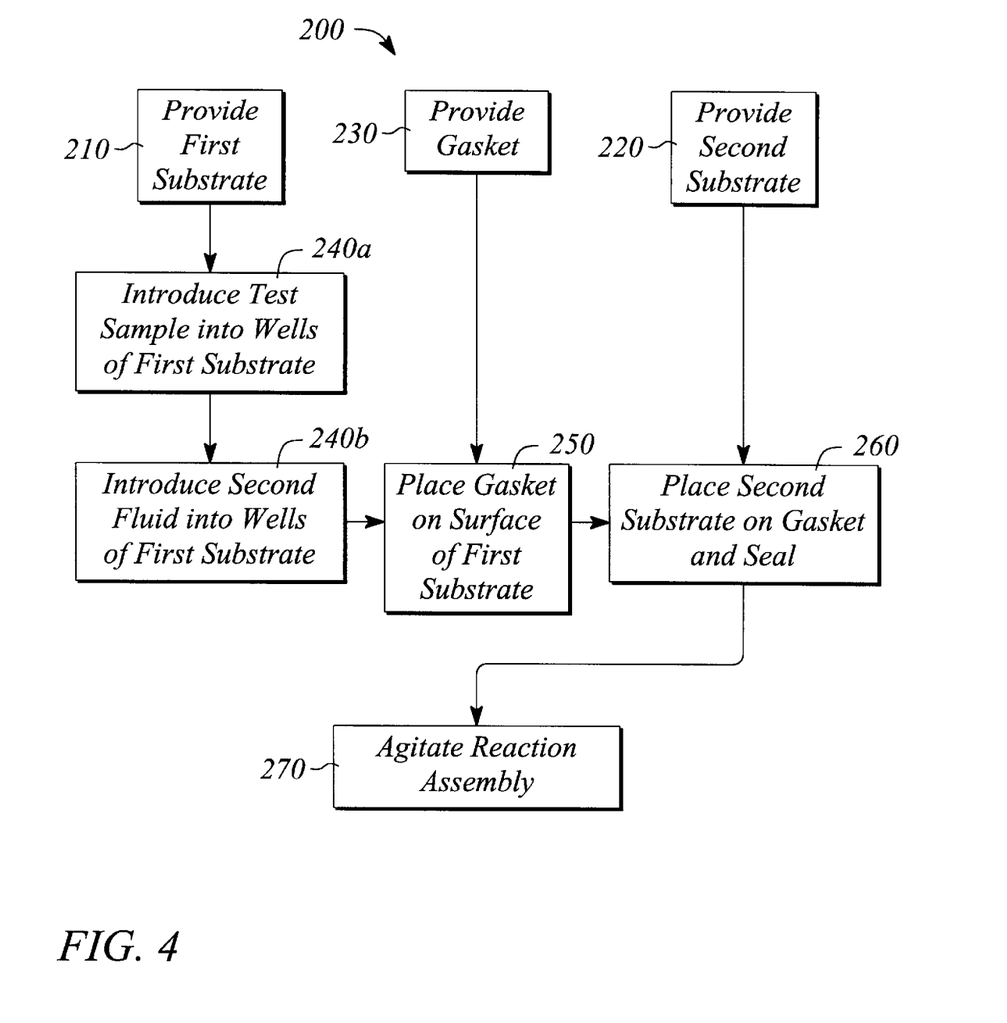
FIG. 4 illustrates a flow chart of another embodiment of the method of the present invention.

A flow chart of the method 200 is illustrated in FIG. 4. Moreover, as mentioned above, FIG. 2 illustrates the components of the reaction assembly apparatus 300 where the seal 131, 131' comprises using the gasket 121, 121'. The method 200 comprises the step of providing 210 a first substrate 101 having a plurality of separately or spatially arranged wells 104 in a surface 102 of the first substrate 101 in a well array pattern. The step of providing 210 and the first substrate 101 are the same as the step of providing 110 and the plate 101, respectively, described above for method 100. See FIG. 2 for the first substrate 101. Each well 104 has an open end 106 at the surface 102 of the first substrate 101, a closed end 105 opposite the open end 106, and a side wall 103 between the closed end 105 and the open end 106. The closed end 105 and the side wall 103 enclose the well on all sides except for the open end 106. The open end 106 provides access to the well 104 for receiving an aliquot of the test chemical sample. Conventional microtiter plates, as mentioned above for method 100, are preferred for the first substrate 101.

The method 200 further comprises the step of providing 220 a plurality of chemical reactants fixed to a surface 112 of a second substrate 113 in an array pattern 111 of features 114. The array 111 of chemical reactant features 114 is spatially arranged on the surface 112 similar to the arrangement of the wells 104 in the first substrate 101. The step of providing 220 and the second substrate 113 are the same as the step of providing 120 and the array substrate 113 described above for method 100. See FIG. 2 for the second substrate 113. In one embodiment, the array 111 is further organized into subarrays 114' of the chemical reactants, as described above for the array 111 in the method 100. Also mentioned above, the chemical reactants at each feature 114 location on the array 111, or in each subarray 114' can be the same, or can be different in at least one feature 114 location on the array 111 (or in at least one subarray 114') or at least one subfeature 115 location within a subarray 114', and still be within the scope of the invention. The second substrate 113 and the array spatial pattern 111 of chemical reactants are matched with the substrate size and well spatial pattern in the first substrate 101, respectively. As mentioned above for method 100, the second substrate 113 can be of any conventional substrate material that is well known in the art and defined above. Further, the second substrate 113 may or may not be flexible or have an adhesive coating to facilitate assembly, as described above for method 100. In a preferred embodiment, the second substrate 113 is optically transparent to facilitate analysis of the results of the chemical reactions.

The method 200 still further comprises the step of providing 230 a gasket 121, 121' having a plurality of spatially arranged through holes 124, 124' with a through hole spacing that is the same as the well spacing and the array feature spacing. Refer to FIG. 2 for an illustration of the gasket 121, 121'. The gasket 121, 121' is made of a pliable or flexible material that can provide a fluid and/or liquid and/or gas tight seal 131, 131' with the application of pressure and further, to prevent unwanted mixing of test samples and chemical reactants. In one embodiment, the gasket 121, 121' may be integral with the surface 102 of the first substrate 101.

Preferably, the gasket 121 provides a seal 131 around each well 104 and each feature 114 or subarray 114', so that the first chemical sample in one well 104 will not mix with the first chemical sample in an adjacent well 104, and further, will not react with an unaligned feature or subarray 114, 114', during a step of mechanically agitating 270, described further below. However, in another embodiment, a seal 131' is provided by a gasket 121' that has at least one through hole 124' that is interconnected with at least one other through hole 124' via channels 125, 125' in the gasket 121', as illustrated in a magnified view of a portion of a major surface of the gasket 121' in FIG. 5. During the step of mechanically agitating 270, the first chemical samples contained in respective wells 104 that are aligned with the interconnected through holes 124' will mix together and react with features or subarrays 114, 114' that are aligned with the interconnected through holes 124', as is further described below.

In addition to the flexible or pliable gasket material, in still another embodiment, the seal 131, 131' may further comprise an adhesive on at least one of the major surfaces of the gasket 121, 121' to facilitate assembly (steps 250, 260, as described below). The adhesive surfaces can be applied as a coating or the like, using an adhesive selected from those described above for the method 100. Alternatively, the gasket 121, 121' itself can be made of a flexible adhesive film that may or may not have reinforcing material, such as a fiber mesh, similar to the adhesive films or tapes manufactured for the electronics industry by Ablestik Laboratories, Rancho Dominguez, Calif.

The method 200 yet still further comprises the step of introducing 240a an aliquot of each of the plurality of test samples into individual wells 104 of the first substrate 101, and further introducing 240b a second fluid to each well. The test samples are a fluid and the aliquot partially fills a volume of the wells 104. The second fluid has a mass density different from a mass density of the test samples. The second fluid further has a low static miscibility with the test samples and does not adhere to or interact with the array substrate or its bound chemical moieties. While the test sample fluid is the target material to be evaluated and is typically an aqueous solution, the second fluid may be gas, such as air, nitrogen gas, or the like. Advantageously, one or more defoaming agents such as Dow Corning® Q7–2587, 30% Simethicone Emulsion USP from the Dow Corning Corporation of Auburn, Mich. may be added where the second fluid is air in order to prevent persistent air bubbles from forming in the aqueous solution during the step of mechanical agitation 270.

The method 200 still further comprises the step of placing 250 the gasket 121, 121' onto the surface 102 of the first substrate 101, such that the through holes 124, 124' are aligned with respective openings 106 of the wells 104. FIG. 2 illustrates the relative assembly described by the method 200. Where the gasket 121, 121' is integral with the surface 102 of the first substrate 101, this step of placing 250 is omitted. The wells 104 are then capped, covered or enclosed by placing 260 the second substrate over the gasket 121, 121', such that the surface 112 containing the chemical reactants is facing the gasket 121, 121' and the features 114 or subarrays 114' are aligned with respective openings 106 of the wells 104 and the through holes 124, 124'. The capped wells 104 form closed cells or individual reaction chambers 132 of the reaction assembly apparatus 300. FIG. 3 also illustrates a side view of the reaction assembly apparatus 300 according to the method 200. Depending on the embodiment, the reaction assembly apparatus 300 is sealed to provide a gas and/or liquid and/or fluid tight seal 131, 131' by compressing the gasket 121, 121' between the first substrate 101 and the second substrate 113 with mechanical clamps, with external fluid pressure, or with vacuum, or is sealed using an adhesive with the gasket 121, 121', for example.

For both methods 100 and 200, other examples of adhesive seals 131, 131' might be to apply an adhesive around the perimeter of the openings 106 of the wells 104 and/or around the perimeter of the features 114, 114' or the perimeter of each through hole 124, 124' in the gasket 121, 121' (and each channel 125, 125', where applicable) and/or the perimeter of the plate 101 and array 111, or just the perimeter of both major sides of the gasket 121, 121' and still be within the scope of the present invention. For adhesives requiring a cure step to activate the adhesion, after the adhesive is cured any clamps or other application of pressure can be removed. Further, where the reaction assembly apparatus 300 is later disassembled, as mentioned above for the method 100, the adhesive seal 131, 131' can be easily removable or reversible to access the array 111. Adhesives that are compatible with the reaction assembly apparatus 300 and have reduced adhesion with heat, cold or radiation are particularly advantageous for disassembling the reaction assembly apparatus 300 for the method 200 also. Where an adhesive is used for the seal 131, 131' in the method 200, the UV releasable adhesives mentioned above are preferred.

The method 200 yet still further comprises the step of agitating 270 the reaction assembly apparatus 300, so that differences in the mass densities of the test sample and the second fluid cause mixing of the test samples with the chemical reactants in each closed cell 132. Mixing of the test samples and chemical reactants produce reaction products used to evaluate the test samples. In a preferred embodiment, the step of agitating 270 is performed under controlled temperature conditions. Advantageously, mechanical agitation 270 will increase the reaction rate between the test samples and the chemical reactants. Examples of conventional equipment that can provide automatic mechanical agitation for an assay include, but are not limited to, the Lab-Line Model 4625 Titer Plate shaker from subsidiary Barnstead-Thermolyne of Apogent Technologies, Portsmouth, N.H.; the Model 51402-00 Microwell Plate Orbital Shaker with Timer manufactured by the Cole-Parmer Instrument Company of Vernon Hills, Ill.; and Model 400 hybridization incubator with rotisserie built inside for tumbling manufactured by Robbins Scientific of Sunnyvale, Calif.

However, because each chamber 132 in the reaction assembly apparatus 300 is sealed, the present invention can advantageously employ much more violent or intense agitation than the agitation provided by the above standard equipment. The sealed reaction assembly apparatus 300 can be exposed to agitation, which is more on the order of the agitation provided by a one-gallon paint shaker, such as the Speed-I-Mix Model CX Explosion-proof single head power paint shaker made by Fleming Gray Limited of St. George, Ontario, Canada, and available from Certified Technology Inc. of Niagara Falls, N.Y. (see the web site at http://www.certifiedtechnology.com/can/fleming.html). In practice, the present invention most advantageously can use custom-built shaking equipment providing more violent or intense agitation than the standard laboratory equipment, but on a smaller scale than the one-gallon paint shaker.

In one embodiment where the seal 131' comprises the gasket 121', the gasket 121' is used to interconnect closed cells (preferably adjacent cells) to provide fluid communication between the interconnected closed cells during the step of agitation 270. The reaction assembly apparatus 300 can be mechanically agitated 270 with incrementally increasing acceleration, advantageously to effect sequential mixing of the interconnected closed cells formed by the channels 125, 125' in the gasket 121'. Consider, for example, a first cell $132_1$ and a second adjacent cell $132_2$ filled with respective first aqueous samples L and M, and interconnected by a first channel 125 with hydrophobic walls and with a nominal hydraulic diameter designated by a value x, as illustrated in FIGS. 5 and 6. In the presence of gentle agitation with a peak acceleration level $A_1$, the first samples L and M are agitated within the first and second cells 132 respectively, but the first sample L does not enter the second cell $132_2$, nor does the first sample M enter the first cell $132_1$, because the hydrophobic nature of the first channel 125 prevents each of the first samples L and M from transiting the first channel 125. However, as the acceleration due to agitation is next increased to a peak acceleration level $A_2$ that is greater than $A_1$, the inertial forces imparted to the first samples L and M cause them to breach the hydrophobic barrier and transit repeatedly across the first channel 125, causing mixing of the first samples L and M in the first cell $132_1$, and second cell $132_2$, thus facilitating any chemical reaction which may occur between the first samples L and M.

Consider further a third cell $132_3$ adjacent to the second cell $132_2$, the third cell $132_3$ containing a first sample N, and the third cell $132_3$ being interconnected to the second cell $132_2$ by a second channel 125' with hydrophobic walls and with a nominal hydraulic diameter designated by y, where y is less than x. The hydrophobic nature of the second channel 125' prevents the first samples M and N from intermixing under gentle agitation with a peak acceleration level $A_1$. Because the diameter y is less than the diameter x, the hydrophobic nature of the second channel 125' also prevents the contents of the third cell $132_3$ from intermixing with the intermixed first samples L and M in the presence of the agitation with a peak acceleration level $A_2$, which was sufficient to mix the first samples L and M, but insufficient to cause transit of samples across the second channel 125'. However, as the acceleration due to agitation is increased to a peak acceleration level $A_3$, which is greater than acceleration $A_2$, mixing occurs between the first sample N in the third cell $132_3$ and the intermixed first samples L and M, thus facilitating any chemical reaction which may occur between the first sample N and the intermixed first samples L and M.

The above described agitation step 270 using interconnecting channels 125, 125' of different hydraulic diameters x and y can be extended to greater than three interconnected cells. The step of agitating 270 provides a method of sequentially mixing or intermixing samples in the presence of increasing levels of acceleration due to agitation. It will be appreciated by those skilled in the art that the channels 125, 125', which provide a barrier to liquid transit, can also be created using channels with hydrophilic walls rather than hydrophobic walls, as long as the geometry of the hydrophilic walls is such as to provide a potential barrier to liquid intrusion. For a discussion of the physics of liquid and gas behavior in hydrophilic and hydrophobic channels of variable hydraulic diameter, see, for example, European patent application EP 1 014 140 A2, entitled "Capillary Fluid Switch," which is hereby incorporated by reference in its entirety herein. Also, see U.S. Pat. No. 5,472,603 entitled "Analytical Rotor with Dye Mixing Chamber", which is incorporated by reference herein in its entirety.

The reaction products produced in the reaction assembly apparatus 300 by the method 200 can be analyzed in accordance with the invention using techniques and equipment, such as those described above for the step of analyzing 160 in the method 100. For the purposes of the invention, the first chemical sample or test sample is a first biological material, such as an oligonucleotide or polynucleotide, a protein, enzyme, polypeptide, antibody, antigen, ligand, receptor, polysaccharide, carbohydrate, or the like, and the second chemical sample or chemical reactant is a complementary second biological material to the first biological material. Either the first material or the second material is used to evaluate the other. For the purpose of simplifying this discussion, the first biological material will be evaluated by the second biological material in a binding assay, such that complementary oligonucleotides, antibody/antigens, ligand/receptors, and the like, are allowed to interact.

In a more preferred embodiment, the first biological material is a target or test material, such as an antigen or an oligonucleotide or polynucleotide that is to be evaluated by the second biological material, which is a probe, such as an antibody or an oligonucleotide probe having a known makeup or sequence. The antibody probe or oligonucleotide probe is complementary to the target antigen or target oligonucleotide, respectively. A plurality of different probes may be bound to the array substrate 113 in order to extensively evaluate the composition of the target. For oligonucleotide assays, most preferably, there is more than one different target oligonucleotide or different portions of a target polynucleotide to be evaluated and a plurality of different oligonucleotide probes arranged on the array 111 that are used to evaluate the different target oligonucleotides or portions. The different probes of the plurality are complementary to different target oligonucleotides or portions.

Another aspect of the present invention is a kit that comprises one or more of an array 111 of biological features, a plate 101 for introducing a sample under test, a gasket 121, 121', mechanical clamps, an adhesive such as that mentioned above, and a sample biological material for a control experiment. Optionally, the kit further comprises instructions in the form of the method 100, 200 of simultaneously conducting multiple reactions of a test sample using the reaction assembly apparatus 300 of the present invention.

For both methods 100, 200, a user might assemble 140, 250, 260 a prefabricated array 111 of probes with a microtiter plate 101 of target samples (steps 240a, 240b of method 200) into the reaction assembly apparatus 300 of the present invention for a hybridization assay to determine information about the target samples. The user will label the target samples with one or more fluorescent labels, for example, using conventional methods prior to assembly, then contact 150, 270 the probes with the target samples, such as by hybridizing them, and subsequently, interrogate and process the hybridized array 111 to analyze the reaction products using well-known conventional methods and equipment. The interrogation will produce a result. Information about the target sample(s) can be obtained from the results of the interrogation. Interrogation is usually accomplished by a suitable scanner, as described above, which can read or detect the location and intensity of fluorescence (signals) at each feature 114, 115 of the array 111. For example, such a scanner may be similar to the GENEARRAY scanner mentioned above. Results from the interrogation can be analyzed results, such as that conventionally obtained by rejecting a reading for a feature 114, 115 which is below a predetermined threshold and/or forming conclusions based on the pattern read from the array 111 (such as whether or not a particular target sequence may have been present in the sample).

As used herein, the term "user" means an individual, a company or other organization, or an employee, consultant, independent contractor, officer, director, or the like, thereof, and includes an agent of the user, which includes a parent or subsidiary organization of the user or of the agent, a contractor, a subcontractor, a customer, or a vendor of the user or the agent, or the like, for example, who may directly or indirectly benefit from the use of the apparatus 300 and/or the method 100, 200 or the information obtained from using the apparatus 300 and/or method 100, 200 of the present invention. Also, one or more of the users may be a manufacturer or user of the array 111 and/or the plate 101 and still be within the scope of the invention. One user might manufacture or purchase the array 111 and/or the plate 101, that user or another user might assemble the reaction assembly apparatus 300, and either of these users or still another user might perform the hybridization assay 150, 270 at the same or remote locations and still be within the scope of the present invention. Yet another user might perform the interrogation and analysis 160 at a location remote to the hybridization location. The results of the interrogation (analyzed or not) can be forwarded (such as by communication) back to the first-mentioned user, or to another remote location if desired, and received there for further use by the first or second user or still another user. Moreover, the user(s) may be in a location(s) remote to the location where the method 100, 200 is performed or the array 111 is fabricated. A user may communicate or forward the results, or the information obtained from the results, to a location remote to the user's location and still be within the scope of the present invention. A location is "remote" if it is at least a different location, including but not limited to, a different room in a building, a different building, a different city, different state or different country, or if the location is at least one, at least ten, or at least one hundred miles apart, for example. "Communicating" information means transmitting the data representing that information as electrical signals over a suitable communication channel (for example, a private or public network). "Forwarding" information refers to any means of getting that information from one location to the next, whether by physically transporting that information or otherwise (where that is possible) and includes, at least in the case of data, physically transporting a medium carrying the data or communicating the data.

Thus, there have been described a novel method 100, 200 for simultaneously conducting multiple chemical reactions, a reaction assembly apparatus 300 that is used to conduct the multiple reactions and a kit comprising one or more components of the apparatus and method. It should be understood that the above-described embodiments are merely illustrative of the some of the many specific embodiments that represent the principles of the present invention. Clearly, those skilled in the art can readily devise numerous other arrangements without departing from the scope of the present invention.

What is claimed is:

1. A method of simultaneously conducting multiple chemical reactions in a reaction assembly that comprises a microtiter plate of wells containing test samples and an array of sets of chemical reactants comprising the steps of:

assembling the array of sets of chemical reactants to the microtiter plate of test samples such that the array covers open ends in the test sample wells of the microtiter plate to form a plurality of closed cells, each closed cell comprising a set of chemical reactants and a respective test sample;

sealing the microtiter plate to the array to create one or more of a gas tight, a liquid tight, and a fluid tight seal; and mechanically agitating the sealed reaction assembly to contact the test samples with the chemical reactants in each closed cell simultaneously.

2. The method of claim 1, wherein the step of assembling comprises the step of placing a pliable gasket between the microtiter plate and the array, the gasket having an arrangement of through holes that align with the test sample wells and the sets of chemical reactants; and the step of sealing comprises the step of applying one or more of mechanical clamps radiation, heat, external fluid pressure, vacuum and an adhesive to the reaction assembly.

3. The method of claim 2, wherein the gasket further comprises an adhesive on at least one gasket surface that interfaces with the microtiter plate or the array, and wherein the step of sealing further comprises removing the one or more of mechanical clamps, radiation, heat, external fluid pressure, and vacuum after a period of time.

4. The method of claim 3, wherein the adhesive is selected from an ultraviolet (UV) light curable adhesive that has increased adhesion with the application of UV light to the adhesive, and a releasable adhesive that has reduced adhesion with the application of one or more of heat, cold and radiation to the adhesive.

5. The method of claim 2, wherein in the step of placing the gasket, the gasket further has at least one channel that interconnects at least two through holes, such that in the step of assembling, the reaction assembly has at least two closed cells that are interconnected, and wherein in the step of mechanically agitating, the agitation has an acceleration, and the step of mechanically agitating comprises the step of incrementally increasing the acceleration to sequentially mix the test samples of the interconnected closed cells.

6. The method of claim 5, wherein the interconnected closed cells are located adjacent to each other.

7. The method of claim 1, wherein in the step of assembling, the array is made of a flexible material, and wherein in the step of sealing, the array is placed against the microtiter plate using one or more of mechanical clamps, radiation, heat, external fluid pressure, vacuum and an adhesive to seal the reaction assembly.

8. The method of claim 1, wherein in the step of assembling, the array is made of an optically transparent flexible film having an adhesive surface that surrounds the sets of chemical reactants, the adhesive surface being contacted with the microtiter plate.

9. The method of claim 1, wherein in the step of assembling, the array is made of a flexible material having an adhesive on a surface that comprises the sets of chemical reactants, and the adhesive surface is contacted with the microtiter plate, and wherein the step of sealing comprises applying one or more of mechanical clamps, radiation, heat, external fluid pressure, and vacuum to the reaction assembly for a period of time until the adhesive adheres the array to the plate.

10. The method of claim 9, wherein the adhesive is selected from an ultraviolet (UV) light curable adhesive that has increased adhesion with the application of UV light to the adhesive, and a releasable adhesive that has reduced adhesion with the application of one or more of heat, cold and radiation to the adhesive.

11. The method of claim 1, wherein the test sample wells are spatially arranged in a surface of the microtiter plate, each well having a side wall adjacent to a closed end that together enclose the well except for an open end at the surface of the microtiter plate, and wherein the ray comprises an array substrate having the sets of chemical reactants bound to an ray surface of the array substrate in an array pattern of features, the array pattern being similar to the spatial arrangement of test sample wells on the microtiter plate.

12. The method of claim 1, wherein in the step of mechanically agitating a difference in mass densities between the test sample and gas filling any space between the test sample and the set of chemical reactants in each closed cell causes mixing of the test sample with the chemical reactants in each closed cell.

13. The method of claim 1, further comprising the step of analyzing reaction products in the closed cells after the step of mechanically agitating.

14. The method of claim 13, wherein one or both of the microtiter plate and the array is optically transparent.

15. The method of claim 1, further comprising the step of analyzing reaction products after the step of mechanically agitating comprising the steps of:

disassembling the reaction assembly;

rinsing the array; and interrogating the array.

16. The method of claim 1, wherein the microtiter plate is selected from a 96, 234, 384, and 1536 well microtiter plate and the number of sets of chemical reactants on the array match the selected microtiter plate.

17. The method of claim 1, wherein each set of chemical reactants is an array feature that comprises a subarray having the chemical reactants arranged in a subarray pattern of subfeatures, and wherein the chemical reactant is different in at least one feature or in at least one subfeature on the array.

18. The method of claim 1, wherein the test sample is different in at least one well of the microtiter plate.

19. A method of simultaneously conducting multiple chemical reactions between a first chemical sample and a second chemical sample comprising the steps of:

providing a plate having a plurality of wells spatially arranged in a surface of the plate in a well array pattern, each well having a side wall adjacent to a closed end that enclose the well except for an open end that is opposite the closed end and that is adjacent to the plate surface, the plurality of wells for receiving the first chemical sample via the open end;

providing an array of the second chemical sample, the ray comprising sets of the second chemical sample bound to and spatially arranged on a surface of an array substrate in an array pattern of features, the well array pattern being spatially similar to the feature array pattern;

assembling the array onto the plate to form a sealed reaction assembly, such that the surface of the array faces the surface of the plate and encloses the open ends of the plurality of wells to form closed cells, each closed cell comprising the first chemical sample and a respective set of the second chemical sample features, wherein the sealed reaction assembly is one or more of gas tight, liquid tight, and fluid tight; and contacting the first chemical sample with the second chemical sample in each closed cell of the sealed reaction assembly.

20. The method of claim 19, wherein the array substrate is made of a flexible material, and wherein in the step of assembling, the array substrate is contacted with the plate using one or more of mechanical clamps, radiation, heat, external fluid pressure, vacuum and an adhesive to seal the reaction assembly.

21. The method of claim 19, wherein the array substrate is made of an optically transparent flexible film having an adhesive on the surface to which the second chemical samples are bound, the adhesive surrounding the features, and wherein in the step of assembling, the adhesive is contacted with the plate surface to seal the reaction assembly.

22. The method of claim 20, wherein the flexible array substrate further comprises the adhesive on the surface to which the second chemical samples are bound, and wherein in the step of assembling, the adhesive surface of the array is contacted with the plate surface, and the reaction assembly is sealed using one or more of beat, radiation, and pressure.

23. The method of claim 22, wherein the adhesive is selected from a releasable adhesive, such that adhesion is reduced with the application of heat, cold or radiation to the adhesive, and an ultraviolet light (UV) curable adhesive, such that adhesion is increased with the application of UV light to the adhesive.

24. The method of claim 19, wherein the plate further comprises a pliable gasket material integral with the surface of the plate, the gasket comprising a plurality of through holes spatially arranged trough a thickness of the gasket material to correspond with arrangement of the plurality of wells, and wherein in the step of assembling, the surface of the ray is contacted with the integral gasket with one or more of mechanical clamps, radiation, heat, external fluid pressure, vacuum and an adhesive to seal the reaction assembly.

25. The method of claim 24, wherein the integral gasket further has at least one channel that interconnects at least two through holes, such that in the step of assembling, the reaction assembly has at least two closed cells that are interconnected, and wherein in the step of contacting, the first chemical samples in the interconnected closed cells mix with each other and with the second chemical samples in each interconnected closed cell via the channel.

26. The method of claim 19, further comprising the step of providing a gasket having a plurality of through holes spatially ranged through a thickness of the gasket in a through hole array pattern, wherein the well pattern, the array pattern and the through hole pattern are dimensionally and spatially similar, the gasket being made of a pliable material, and wherein the step of assembling comprises placing the pliable gasket between the plate surface and the array surface, such that the plurality of through holes are aligned with the features of the second chemical sample and the wells, and sealing the gasket to the array and the plate using one or more of mechanical clamps, radiation, heat, external fluid pressure, vacuum and an adhesive to seal the reaction assembly.

27. The method of claim 26, wherein the pliable gasket comprises the adhesive on at least one surface adjacent either the plate surface or the array surface.

28. The method of claim 27, wherein the adhesive is selected from a releasable adhesive, such that adhesion is reduced with the application of heat, cold or radiation to the adhesive, and an ultraviolet light (UV) curable adhesive, such that adhesion is increased with the application of UV light to the adhesive.

29. The method of claim 26, wherein in the step of providing the gasket, the gasket further has at least one channel that interconnects at least two through holes, such that in the step of assembling, the reaction assembly has at least two closed cells that are interconnected, and wherein in the step of contacting, the first chemical samples in the interconnected closed cells mix with each other and with the second chemical samples in each interconnected closed cell via the channel.

30. The method of claim 19, wherein the step of contacting comprises one or more of mechanically agitating the reaction assembly, controlling the reaction temperature of the reaction assembly, directing radiation into the assembly, and inverting the reaction assembly to cause mixing between the first chemical sample and the second chemical sample.

31. The method of claim 19, before the step of assembling, further comprising the steps of:
providing a gasket having a plurality of spatially arranged through holes, the arrangement of through holes being similar to the arrangement of the wells and of the array pattern, the gasket being made of a pliable material; and
introducing an aliquot of the first chemical sample into each well of the plate, the first chemical samples being fluid and partially filling the wells, and introducing a volume of a second fluid to the wells, the second fluid having a mass density that is different from a mass density of the first chemical sample and the second fluid being non-reactive with the first chemical sample and second chemical sample,
wherein the step of assembling comprises the steps of:
placing the gasket on the surface of the plate,
placing the array on the gasket, such that the array features are aligned with the through holes and the wells, and
sealing the plate, the gasket and the array together using one or more of mechanical clamps, radiation, heat, external fluid pressure, vacuum and an adhesive,
and wherein the step of contacting comprises mechanically agitating the reaction assembly to mix the first chemical sample and the second chemical sample in each closed reaction cell.

32. The method of claim 31, wherein in the step of mechanically agitating, the difference in the mass densities of the first chemical sample and the second fluid causes mixing of the first chemical sample with the second chemical sample in each closed cell.

33. The method of claim 31, wherein in the step of providing the gasket, the gasket further has at least one channel that interconnects at least two through holes, such that in the step of assembling, the reaction assembly has at least two closed cells that are interconnected, and wherein in the step of mechanically agitating, the agitation has an acceleration, and the step of mechanically agitating comprises incrementally increasing the acceleration in magnitude to sequentially mix the first chemical samples of the interconnected closed cells.

34. The method of claim 33, wherein the interconnected closed cells are located adjacent to each other.

35. The method of claim 31, wherein the gasket further comprises the adhesive on surfaces that interface with the plate and the array, and wherein the step of sealing further comprises removing the one or more of mechanical clamps, radiation, heat, external fluid pressure, and vacuum after a period of time.

36. The method of claim 35, wherein the gasket is made of a flexible adhesive film.

37. An apparatus for simultaneously conducting multiple chemical reactions comprising:
a plate having a plurality of wells spatially arranged in a surface of the plate in a well array pattern, each well having a side wall adjacent to a closed end that enclose the well except for an open end that is opposite the closed end and that is adjacent to the plate surface, the plurality of wells for receiving a test sample via the open end;
an array of sets of chemical reactants, the sets of chemical reactants being bound to and spatially arranged on a surface of an array substrate in an array pattern of features, the well array pattern being spatially similar to the feature array pattern, wherein the array surface faces the plate surface and covers the open ends of the wells to form closed cells, each closed cell comprising a respective test sample and a respective set of the chemical reactants; and
a seal between the plate and the array that is one or more of gas tight, liquid tight, and fluid tight.

38. The apparatus of claim 37, wherein the seal comprises a pliable gasket and one or more of mechanical clamps, radiation, heat, external fluid pressure, vacuum and an adhesive, the gasket having a plurality of through holes spatially arranged through a thickness of the gasket in a through hole pattern that is dimensionally and spatially similar to the well pattern and the array pattern.

39. The apparatus of claim 38, wherein the pliable gasket is a flexible adhesive film.

40. The apparatus of claim 38, wherein the pliable gasket further has at least one channel that interconnects at least two through holes, such that the respective test samples in the interconnected closed cells can be mixed via the channel.

41. The apparatus of claim 38, wherein the pliable gasket is integral with the surface of the plate.

42. The apparatus of claim 37, wherein the seal comprises the array substrate being made of a flexible material and one or more of mechanical clamps, radiation, heat, external fluid pressure, vacuum and an adhesive.

43. The apparatus of claim 37, wherein the seal comprises the array substrate being made of an optically transparent flexible film having an adhesive that surrounds the features on the array surface, the adhesive being contacted with the plate surface.

44. The apparatus of claim 37, wherein the seal comprises using an adhesive selected from a releasable adhesive, such that adhesion is reduced with the application of heat, cold or radiation to the adhesive, and an ultraviolet light curable adhesive, such that adhesion is increased wit the application of ultraviolet light to the adhesive.

45. The apparatus of claim 44, wherein the releasable adhesive is an ultraviolet light-releasable adhesive.

46. The apparatus of claim 41, wherein in the plate is a microtiter plate selected from a 96, 234, 384, and 1536 well plate, and wherein the array has the array pattern that matches the selected microtiter plate.

47. A kit for simultaneously conducting multiple different assays of biological materials comprising:
- an array having a plurality of sets of chemical reactants spatially arranged on an may substrate; and
- a plate having a plurality of spatially arranged wells in the plate, the wells being closed at one end and open at an opposite end for receiving a sample under test,
- wherein the array and the plate form a multiple closed cell reaction assembly when the array is assembled to the plate, such that the array covers the open ends of the wells to form closed cells, each closed cell comprising the test sample and a respective set of the chemical reactants, the reaction assembly comprising a seal between the plate and the array that is one or more of gas tight, liquid tight, and fluid tight when assembled.

48. The kit of claim 47, further comprising one or more of:
- a pliable gasket having a plurality of spatially arranged through holes similar to the spatial arrangement of the wells and the sets of reactants, the pliable gasket providing the seal between the plate and the array when combined wit one or more of mechanical clamps, radiation, heat, external fluid pressure, vacuum and an adhesive;
- an adhesive for sealing at least the array and the plate;
- a sample biological material for a control experiment;
- instructions for simultaneously conducting multiple reactions; and
- instructions for assembling the array to the plate.

49. A method of simultaneously conducting multiple chemical reactions in a reaction assembly that comprises a microtiter plate of wells containing test samples and an may of sets of chemical reactants comprising the steps of:
- assembling the array of sets of chemical reactants to the microtiter plate of test samples such that the may covers open ends in the test sample wells of the microtiter plate to form a plurality of closed cells, each closed cell comprising a set of chemical reactants and a respective test sample, the sets of chemical reactants being bound to an array surface of the array;
- sealing the microtiter plate to the array to create one or more of a gas tight, a liquid tight, and a fluid tight seal; and
- mechanically agitating the sealed reaction assembly to contact the test samples with the array-bound chemical reactants in each closed cell simultaneously.

* * * * *